United States Patent
Weitzel et al.

(10) Patent No.: US 6,913,588 B2
(45) Date of Patent: *Jul. 5, 2005

(54) EXTRACORPOREAL FLUID CIRCUIT AND RELATED METHODS

(75) Inventors: William Frederick Weitzel, Ypsilanti, MI (US); H. David Humes, Ann Arbor, MI (US); Emil Presley Paganini, Chesterland, OH (US); Deborah Ann Buffington, Ann Arbor, MI (US); Angela J. Funke, Ann Arbor, MI (US)

(73) Assignees: Nephros Therapeutics, Inc., Lincoln, RI (US); The Regents of the University of Michigan, Ann Arbor, MI (US)

(*) Notice: Subject to any disclaimer, the term of this patent is extended or adjusted under 35 U.S.C. 154(b) by 104 days.

This patent is subject to a terminal disclaimer.

(21) Appl. No.: 10/402,912

(22) Filed: Mar. 28, 2003

(65) Prior Publication Data

US 2004/0024342 A1 Feb. 5, 2004

Related U.S. Application Data

(63) Continuation of application No. 09/553,722, filed on Apr. 21, 2000, now Pat. No. 6,561,997.
(60) Provisional application No. 60/130,688, filed on Apr. 23, 1999.

(51) Int. Cl.$^7$ ............................ A61M 37/00; C02F 1/44
(52) U.S. Cl. ............... 604/6.09; 604/4.01; 604/5.01; 604/5.04; 604/6.06; 604/6.11; 210/645; 210/646
(58) Field of Search .................... 604/4–5, 7–8, 604/6.09, 6.11, 5.01, 6.06, 6.16; 422/44–48; 210/57, 650, 645–647, 195.2

(56) References Cited

U.S. PATENT DOCUMENTS

| | | |
|---|---|---|
| 4,209,391 A | 6/1980 | Lipps et al. |
| RE30,724 E | 8/1981 | Klayum et al. |
| 4,435,127 A | 3/1984 | Kränzle et al. |
| 4,500,309 A | 2/1985 | Diederich et al. |
| 4,540,399 A | 9/1985 | Litzie et al. |
| 4,618,343 A | 10/1986 | Polaschegg et al. |
| 4,658,655 A | 4/1987 | Kanno |
| 4,828,543 A | 5/1989 | Weiss et al. |
| 4,844,810 A | 7/1989 | Richalley et al. |
| 4,855,057 A | 8/1989 | Ohnishi et al. |
| 4,863,590 A | 9/1989 | Ohnishi et al. |

(Continued)

FOREIGN PATENT DOCUMENTS

| | | |
|---|---|---|
| EP | 0 490 212 A1 | 6/1992 |
| EP | 0 796 997 A1 | 9/1997 |
| FR | 2 686 255 | 7/1993 |
| FR | 2 702 962 | 9/1994 |
| WO | WO 00/64510 | 9/2000 |

OTHER PUBLICATIONS

Ahmad et al. (1988), "Center and Home Chronic Hemodialysis" in *Disease of the Kidney* (Schrier RW and Goffschalk CW eds.), 4$^{th}$ Ed., Boston: Little, Brown and Co., 3281–3319, 3322–3329, 3332–3343.

(Continued)

*Primary Examiner*—Angela D. Sykes
*Assistant Examiner*—Leslie R. Deak
(74) *Attorney, Agent, or Firm*—Goodwin Procter, LLP

(57) ABSTRACT

A circuit for extracorporeal treatment of a body fluid, the circuit including in serial fluidic communication an inlet for receiving the body fluid from a patient, a first pump, a first treatment device for processing the body fluid, a second pump, an outlet for returning processed body fluid to the patient; and a shunt. The shunt is upstream from the first pump and downstream from the second pump.

20 Claims, 4 Drawing Sheets

U.S. PATENT DOCUMENTS

| | | | |
|---|---|---|---|
| 4,897,184 | A | 1/1990 | Shouldice et al. |
| 4,925,555 | A | 5/1990 | Spielberg |
| 4,950,225 | A | 8/1990 | Davidner et al. |
| 5,062,442 | A | 11/1991 | Stenstrom et al. |
| 5,069,662 | A | 12/1991 | Bodden |
| 5,368,555 | A | 11/1994 | Sussman et al. |
| 5,411,479 | A | 5/1995 | Bodden |
| 5,429,938 | A | 7/1995 | Humes |
| 5,470,483 | A | 11/1995 | Bene et al. |
| 5,476,444 | A | 12/1995 | Keeling et al. |
| 5,549,674 | A | 8/1996 | Humes et al. |
| 5,630,946 | A | 5/1997 | Hart et al. |
| 5,647,984 | A | 7/1997 | Hovland et al. |
| 5,686,289 | A | 11/1997 | Humes et al. |
| 5,690,831 | A | 11/1997 | Kenley et al. |
| 5,725,492 | A | 3/1998 | Igo et al. |
| 5,776,091 | A | 7/1998 | Brugger et al. |
| 5,813,842 | A | 9/1998 | Tamari |
| 5,814,004 | A | 9/1998 | Tamari |
| 5,817,046 | A | 10/1998 | Glickman |
| 6,060,270 | A | 5/2000 | Humes |
| 6,150,164 | A | 11/2000 | Humes |
| 6,561,997 | B1 | 5/2003 | Weitzel et al. |

OTHER PUBLICATIONS

Avissar et al. (Feb. 1994), "Human Kidney Proximal Tubules are the Main Source of Plasma Glutahione Peroxidase," *American Journal of Physiology*, 266(2):C367–C375.

Bacallao et al. (1989), "Molecular events in the Organization of Renal Tubular Epithelium: from Nephrogenesis to Regeneration," *American Physiological Society*, 257:F913–F924.

Bäckman et al. (1988), "Glutahione Transferase in the Urine: A Market for Post–Transplant Tubular Lesions," *Kidney Int'l.*, 33:571–577.

Beutler (ed.) (1984), "Glutathione Peroxidase (GSH–Px)," in *Red Cell Metabolism: A Manual of Biochemical Methods*, 3$^{rd}$ Edition, Grune & Stratton, New York, pp. 74–76.

Bhalla (1989), "Hormones and the Immune Response," *Annals of the Rheumatic Diseases*, 48(1):1–6.

Bikle et al. (1992), "Clinical Counterpoint: Vitamin D: New Actions, New Analogs, New Therapeutic Potential," *Endocrine Reviews*, 13(4):765–784.

Calne (Dec. 1970), "Organ Transplantation Between Widely Disparate Species," *Transplantation Proceedings*, 2(4):550–556.

Cieslinski (Aug. 1, 1995), "Excerpt from Phase I Grant Application entitled, 'Tissue Engineering of a Biohybrid Human Kidney Tubule,'" *Small Business Program Phase I Grant Application*, No. SBIR 94–3, pp. 1–2, 4, 10–24.

Cieslinski (Aug. 1, 1996), "Excerpt from Phase II Grant Application entitled, 'Bioartificial Renal Tubule for Renal Failure Therapy,'" *Small Business Program Phase II Grant Application*, Solicitation No. DK–50539, pp. 1, 13–40.

Cieslinski et al. (Mar. 25, 1994), "Tissue Engineering of a Bioartificial Kidney," *Biotechnology and Bioengineering*, 43(7):678–681.

Cooper et al. (1991), "The Pig as Potential Organ Donor for Man," in *Xeno–Transplantation* (Cooper et al. eds.), Springer, Berlin, Chapter 30, pp. 481–500.

Cozzi et al. (Sep. 1995), "The Generation of Transgenic Pigs as Potential Organ Donors for Humans," *Nature Medicine*, 1(9):964–966.

Curthoys (1983), "Role of γ–Glutamyltranspeptidase in the Renal Metabolism of Glutathione," *Mineral and Electrolyte Metabolism*, 9:236–245.

Deneke et al. (Oct. 1989), "Regulation of Cellular Glutahione," *American Journal of Physiology*, 257(4):L163–L173.

Dröge et al. (Nov. 1994), "Functions of Glutathione and Glutathione Disulfide in Immunology and Immunopathology," *The FASEB Journal*, 8(14):1131–1138.

Fleck (1992), "Renal Transport of Endogenous Amino Acids," *Renal Physiol Biochem*, 15:257–276.

Fonteles et al. (1976), "Extraction of Glutathione by the Isolated Perfused Rabbit Kidney," *Journal of Surgical Research*, 21:169–174.

Frank et al. (1993), "Human Renal Tubular Cells as Cytokine Source: PDGF–B, GM–CSF and IL–6 mRNA Expression In Vitro," *Exp Nephrol*, 1:26–35.

Galley et al. (1996), "The Immuno–Inflammatory Cascade", *British Journal of Anasethesia*, 77:11–16.

Gillin et al. (1993), "Urea Transport in the Kidney," *Seminars in Nephrology*, 13(2):146–154.

Goode et al. (1993), "Free Radicals and Antioxidants in Sepsis", *Critical Care Medicine*, 21(11):1770–1776.

Hall et al. (1989), "Stem Cells: The Generation and Maintenance of Cellular Diversity," *Development*, 106:619–633.

Hammerman et al. (1993), "The Growth Hormone Insulin–Like Growth Factor Axis in Kidney Revisited," *American Physiological Society*, 265:F1–F14.

Howard et al. (Apr. 1993), "Interleukin 10 Protects Mice From Lethal Endotoxemia." *J. Exp. Med.*, 177(4):1205–1208.

Humes (1995), Abstract of "Cell Therapy for Erythropoietin (EPO) Deficient Anemias," *Dialysis: Complications/Outcomes*, J.A.S.N. 6:535.

Humes (1995), "Tissue Engineering of the Kidney," in *The Biomedical Engineering Handbook*, (Joseph D. Bronzino ed.–in–chief), CRC Press, Boca Raton, Chapter 121, 1807–1824.

Humes (1995), Abstract of "Tissue Engineering of a Bioartificial Hemofilter," *Dialysis: Access/Methods of Hemodialysis*, J.A.S.N. 6:492.

Humes (Aug. 1996), "Tissue Engineering of a Bioartificial Kidney: A Universal Donor Organ," *Transplantation Proceedings*, 28(4):2032–2035.

Humes et al. (1995), Abstract of "Tissue Engineering of a Bioartificial Renal Tubule," *J.A.S.N.*, 6(3):465.

Humes (1995), Abstract of "Tissue Engineering of a Biohybrid Kidney Filter and Kidney Tubule," *Journal of Cellular Biochemistry*, Abstract Supplement 0(21B):9.

Humes (1997), "Application of Cell and Gene Therapies in the Tissue Engineering of Renal Replacement Devices," in *Principles of Tissue Engineering* (Lanza et al. eds.), R.G. Landes Company, Austin Texas, Chapter 35, 577–589.

Humes (1996), "The Bioartificial Renal Tubule: Prospects to Improve Supportive Care in Acute Renal Failure," *Renal Failure*, 18(3):405–408.

Humes (1995), "Acute Renal Failure: Prevailing Challenges and Prospects for the Future," *Kidney International*, 48, Suppl. 50:S–26—S-32.

Humes et al. (Feb. 1995), "Prospects for an Implantable Bioartificial Kidney," *Contemporary Dialysis & Nephrology*, 16(2):24–27.

Humes et al. (Jul. 1996), "Tubulogenesis From Isolated Single Cells of Adult Mammalian Kidney: Clonal Analysis with a Recombinant Retrovirus," *American Journal of Physiology*, 271(1):F42–F49.

Humes et al. (Jul. 1992), "Interaction Between Growth Factors and Retinoic Acid in the Induction of Kidney Tubulogenesis in Tissue Culture," *Experimental Cell Research*, 201(1):8–15.

Humes et al. (1980), "Ionophore A23187 Induced Reductions in Toad Urinary Bladder Epithelial Cell Oxidative Phosphorylation and Viability," *Pflügers Arch.*, 388:217–220.

Humes et al. (May 1999), "Replacement of Renal Function in Uremic Animals with a Tissue–Engineered Kidney," *Nature Biotechnology*, 17(5):451–455.

Imai et al. (1974), "Transtubular Oncotic Pressure Gradients and Net Fluid Transport in Isolated Proximal Tubules," *Kidney International*, 6:138–145.

Ip et al. (1988), "Cellular Control of Membrane Permeability Implications for a Bioartificial Renal Tubule," *Trans Am Soc Artif Intern Organs*, 34:351–355.

Jamison et al. (1995), "Renal Handling of Organic Compounds," in *Massry & Glassock's Textbook of Nephrology* (Jonathan W. Pine, Jr. ed.), vol. 1, $3^{rd}$ Edition, Williams & Wilkins, Baltimore, Chapter 7, Part I, pp. 87–90.

Jevnikar et al. (1991), "Stimulated Kidney Tubular Epithelial Cells Express Membrane Associated and Secreted TNFα," *Kidney International*, 40:203–211.

Kida et al. (Oct. 1978), "Renal Net Glucose Release In Vivo and Its Contribution to Blood Glucose in Rats," *Journal of Clinical Investigation*, 62(4):721–726.

Kinne et al. (1992), "Renal Plasma Membranes: Isolation, General Properties, and Biochemical Components," in *Handbook of Physiology—Section 8: Renal Physiology* (Erich E. Windhager ed.), Oxford University Press, New York, vol. II, Chapter 45, 2083–2117.

Kinscherf et al. (Apr. 1994), "Effect of Glutathione Depletion and Oral N–acetyl–cysteine Treatment on $CD4^+$ and $CD8^+$ Cells," *The FASEB Journal*, 8(6):448–451.

Kjellstrand et al (1988), "Treatment of Acute Renal Failure," in *Diseases of the Kidney* (Schrier RW and Goffschalk CW eds.), $4^{th}$ Ed., Little, Brown and Co., Boston, Chapter 52, 1501–1540.

Kopple (1995), "Nutritional Management," *Massry & Glassock'sTextbook of Nephrology* (Jonathan W. Pine, Jr. ed.), vol. 2, $3^{rd}$ Edition, Williams & Wilkins, Baltimore, Chapter 82, 1499–1512.

Koren et al. (1992), "Peripheral Blood Mononuclear Cells: A Model for the Human Vitamin D Endocrine System in Health and Disease," *Molecular and Cellular Endocrinology*, Elsevier Scientific Publishers Ireland, Ltd., 83:C9–C12.

Kreuzer (1982), "Oxygen supply to tissues: The Krogh model and its assumptions," *Experientia*, Birkhäuser Verlag, Basel/Switzerland, 38:1415–1426.

Krogh (1919), "The Number and Distribution of Capillaries in Muscles with Calculations of the Oxygen Pressure Head Necessary for Supplying the Tissue," *J. Physiol.*, London, 52:409–415.

Langer et al. (1993), "Tissue Engineering," *Science*, 260:920–926.

Lash et al. (Jul. 1986), "Exogenous Glutathione Protects Intestinal Epithelial Cells From Oxidative Injury," *Proc. Natl. Acad. Sci. USA*, 83:4641–4645.

Liu et al. (1993), "Cellular and molecular aspects of renal repair in acute renal failure," *Current Opinion in Nephrology & Hypertension*, 2:618–624.

Lordon et al. (Aug. 1972), "Post–Traumatic Renal Failure in Military Personnel in Southeast Asia," *The American Journal of Medicine*, 53:137–147.

Maack et al. (1992), "Renal Handling of Proteins and Polypeptides," in *Handbook of Physiology—Section 8: Renal Physiology* (Erich E. Windhager ed.), Oxford University Press, New York, vol. II, Chapter 44, 2039–2082.

MacKay et al. (1998), "Tissue Engineering of a Bioartificial Renal Tubule," *ASAIO Journal*, 44(3):179–183.

Macias et al. (1991), "Continuous Venovenous Hemofiltration: An Alternative to Continuous Arteriovenous Hemophiltration and Hemodiafiltration in Acute Renal Failure," *American Journal of Kidney Diseases*, 28(4):451–458.

Merzkirch (1987), *Flow Visualization*, $2^{nd}$ ed., Academic Press, Orlando, pp. 17–24.

Mitch (Dec. 1981), "Amino–Acid Release From the Hindquarter and Urea Appearance in Acute Uremia," *American Journal of Physiology: Endocrinology and Metabolism*, 4(6):E415–E419.

Mohandas et al. (1984), "Differential Distribution of Glutathione and Glutathione–Related Enzymes in Rabbit Kidney," *Biochemical Pharmacology*, 33(11):1801–1807.

Montemurro et al. (1960), "Survival and body composition of normal hypothalamic obese rats in acute starvation," *American Journal of Physiology*, 198(4):757–761.

Ong et al. (Feb. 1994), "Tubular–Derived Growth Factors and Cytokines in the Pathogenesis of Tubulointerstitial Fibrosis: Implications for Human Renal Disease Progression," *American Journal of Kidney Diseases*, 23(2):205–209.

Omstad et al. (1982), "Evidence for Different Localization of Glutathione Oxidase and γ–Glutamyltransferase Activities During Extracellular Glutathione Metabolism in Isolated Perfused Rat Kidney," *Biochimica et Biophysica Acta*, 700:148–153.

Parekh et al. (1973), "Physical and Chemical Properties of Some Dyes Suitable for Renal Passage Time Measurements," *Pflügers Arch*, 343:1–9.

Pitts (Jul. 20, 1945), "The Renal Regulation of Acid Base Balance with Special Reference to the Mechanism for Acidifying the Urine," *Science*, 102(2638):49–54; 81–85.

Potten et al. (Dec. 1990), "Stem Cells: Attributes, Cycles, Spirals, Pitfalls and Uncertainties Lessons For and From the Crypt," *Development*, 110(4):1001–1020.

Ross et al. (1997), "Low Whole Blood and Erythrocyte Levels of Glutathione in Hemodialysis and Peritoneal Dialysis Patients," *American Journal of Kidney Diseases*, 30(4):489–494.

Rotem et al. (1993), "Oxygen is a Factor Determining In Vitro Tissue Assembly: Effects on Attachment and Spreading of Hepatocytes," *Biotechnology and Bioengineering*, 43:654–660.

Roth et al. (1973), "Column Chromatography of Amino Acids With Fluorescence Detection," *J. Chromatography*, Elsevier Scientific Publishing Company, Amsterdam, 83:353–356.

Shatford et al. (1992), "Hepatocyte Function in a Hollow Fiber Bioreactor: A Potential Bioartificial Liver," *Journal of Surgical Research*, 53:549–557.

Sielaff et al. (1995), "Gel–Entrapment Bioartificial Liver Therapy in Galactosamine Hepatitis," *Journal of Surgical Research*, 59:179–184.

Silbernagel (1983), "Kinetics and Localization of Tubular Resorption of "Acidic" Amino Acids A Microperfusion and Free Flow Micropuncture Study in Rat Kidney," *Pflügers Arch*, 396:218–224.

Spring (1983), "Fluid Transport by Gallbladder Epithelium," *J. Exp. Bio.*, The Company of Biologists Limited, Great Britain, 106:181–194.

Stadnyk (Oct. 1994), "Cytokine Production by Epithelial Cells," *The FASEB Journal*, 8:1041–1047.

Standiford et al. (Aug. 1997), "Cytokines in Host Defense Against Pneumonia," *Journal of Investigative Medicine*, 45(6):335–345.

Standiford et al. (Aug. 15, 1995), "Neutralization of IL–10 Increases Lethality in Endotoxemia," *The Journal of Immunology*, 155(4):2222–2229.

Sullivan et al. (1989), "An Elevation in the Concentration of Free Cytosolic Calcium is Sufficient to Activate the Oxidative Burst of Granulocytes Primed with Recombinant Human Granulocyte–Marcophage Colony–Stimulating Factor," *Journal of Biological Chemistry*, 264(11):6302–6309.

Sussman et al. (May 1994), "The Hepatix Extracorporeal Liver Assist Device: Initial Clinical Experience," *Artificial Organs*, 18(5):390–396.

Tannen et al. (Jan. 1984), "Response of Ammonia Metabolism to Acute Acidosis," *Kidney Int.*, 25(1):1–10.

Tannen et al. (1979), "Ammoniagenesis by the Isolated Perfused Rat Kidney: The Critical Role of Urinary Acidification," *Clinical Science*, 56:353–364.

Thadhani et al. (May 30, 1996), "Acute Renal Failure," *New England Journal of Medicine*, 334(22):1448–1460.

Toback (1992), "Regeneration After Acute Tubular Necrosis," *Kidney International*, 41:226–246.

Watanabe et al. (May 1997) "Clinical Experience with a Bioartificial Liver in the Treatment of Severe Liver Failure: A Phase I Clinical Trial," *Annals of Surgery*, 225(5):484–494.

Weinberg et al. (1982), "Mitochondrial Bioenergetics during the Initiation of Mercuric Chloride–induced Renal Injury," *The Journal of Biological Chemistry*, 257(1):60–67.

Weitzel et al. (1998), Abstract of "Analysis of a Renal Proximal Tubule Assist Device (RAD) During CVVH on Uremic Dogs," *American Society of Nephrology*, $31^{st}$ Annual Meeting, Oct. 25–28, 1998.

Whelton et al. (Feb. 1969), "Post–Traumatic Acute Renal Failure in Vietnam," *Johns Hopkins Med. J.*, 124(2):95–105.

Yang, ed. (1989), "Medicine and Biology," in *Handbook of Flow Visualization*, Hemisphere Publishing Corporation, Washington, D.C., Chapter 36, pp. 603–618.

Yang et al. (May 15, 1993), "Vitamin D Deficiency Suppresses Cell–Mediated Immunity In Vivo," *Archives of Biochemistry and Biophysics*, 303(1):98–106.

International Search Report for International Patent Application No. PCT/US00/10885, 6 pages, Aug. 10, 2000.

Zimmerman, (Apr. 1995), "Defining the Role of Oxyradicals in the Pathogenesis of Sepsis," *Critical Care Medicine*, 23(4):616–617.

EXTRACORPOREAL FLUID CIRCUIT AND RELATED METHODS

CROSS-REFERENCE TO RELATED APPLICATIONS

The present application is a continuation of U.S. Ser. No. 09/553,772, filed Apr. 21, 2000 now U.S. Pat. No. 6,561,997, which claims priority to and the benefit of U.S. provisional patent application Ser. No. 60/130,688, filed Apr. 23, 1999. The entire disclosure of each of these applications is incorporated herein by reference.

GOVERNMENT RIGHTS

This invention was made with Government support under SBIR Grant No. DK 50539-03. The Government may have certain rights in the invention.

TECHNICAL FIELD

The invention relates generally to extracorporeal circuits for removing and returning a patient's bodily fluids. More specifically, the invention relates to a geometries for an extracorporeal circuit for providing treatment to a patient's bodily fluids with an artificial organ.

BACKGROUND INFORMATION

Patients with compromised organ function are often treated by using an external artificial organ. For example, an external hemofiltration or dialysis system is typically used to remove waste products from the blood of a patient with compromised kidney function. Blood is removed from the patient, processed in the system, and returned to the patient. Typically, blood is removed through an extracorporeal circuit, generally consisting of tubing and a device to propel the blood. Many extracorporeal circuits have various processing devices disposed throughout the circuit.

Bioartificial organs provide additional benefits in an extracorporeal circuit by performing functions that promote proper homeostasis and that compensate for dysfunction of the natural organ. However, bioartificial organs, in-contact with a bodily fluid, often contain living cells that require precise control of temperature, pressure, and flow rate of the fluid in order to maintain their metabolic activity. Typical circuits do not provide optimal control over these important parameters. Accordingly, there is a need in the art for improved extracorporeal fluid circuits that provide optimal control over flow rate, temperature, and pressure within the circuit.

SUMMARY OF THE INVENTION

The present invention provides extracorporeal circuits for use in treating a body fluid. Circuits of the invention have a circuit geometry adapted to provide precise control of flow rate, temperature, and pressure through the circuit. Extracorporeal circuits of the invention produce significant advantages, particularly when used in connection with a bioartificial organ, or other fluid circuits. For example, circuits of the invention provide a "shunting" mechanism for fluids if, for example, a blockage occurs in the circuit or in a component with which the circuit is in communication. The shunting mechanism also allows for circuits of the invention to be rapidly attached to and detached from other components or circuits without substantial interruption of fluid flow.

In one aspect of the invention, a circuit for extracorporeal treatment of a body fluid comprises, in serial fluidic communication, an inlet for receiving a body fluid from a patient, a first pump, a first treatment device for processing the body fluid, a second pump, an outlet for returning processed body fluid to the patient and a shunt. The shunt is upstream from the first pump and downstream from the second pump.

In one embodiment of the invention, body fluid is altered prior to entering the inlet. Also in certain embodiments, the shunt connects the inlet to the outlet. A circuit of the invention can include a second treatment device upstream from the inlet, and can include a third pump upstream from the second treatment device. A connector can be disposed between the inlet and the shunt and/or between the outlet and the shunt. The inlet and/or outlet can be a conduit. The inlet, outlet, and/or connector are optionally disposable.

In certain embodiments described above, the first treatment device performs at least one function of a human organ and is preferably a renal assist device. The shunt typically is situated in parallel with the first treatment device. Also, a supply line in fluidic communication with the first treatment device can be added for delivering an additional fluid to the first treatment device. A supply pump can be placed in fluidic communication with the supply line for pumping the additional fluid into the first treatment device. At least a portion of the body fluid receivable within the inlet and at least a portion of the additional fluid receivable within the supply line can combine within the first treatment device. At least one of the fluids can be altered within the first treatment device. A waste receptacle can be in fluidic communication with the first treatment device. At least one heating device can be in association with the circuit. An anticoagulant (for example, but without limitation, heparin) infuser can be in fluidic communication with the circuit. At least one pressure monitor can be in association with the circuit. At least one flow monitor can be in association with the circuit. The pumps can have a pumping rate from about 10 ml/min to about 1000 ml/min. The first pump can have a pumping rate that differs from a second pumping rate of the second pump by a value ranging from about 1 ml/min to about 200 ml/min.

In another aspect of the invention, a method for treating a patient with a compromised bodily function includes the steps of providing a circuit, removing a body fluid from the patient, moving the body fluid through the circuit for processing, and returning processed body fluid to the patient. A preferred circuit is described above and can have any of the features described above. In one embodiment, the compromised bodily function is renal abnormality, the body fluid is blood and/or the body fluid is a blood filtrate.

In another aspect of the invention, a circuit for extracorporeal treatment of a body fluid includes a first section which includes, in serial fluidic communication, an inlet for receiving a body fluid from a patient, a first treatment device for processing the body fluid, a first pump, an outlet for returning processed body fluid to the patient, and a shunt. The shunt connects the inlet with the outlet. The circuit also includes a second section comprising, in serial fluidic communication, a first conduit for receiving an additional fluid, a second pump, the first treatment device for processing the additional fluid, and a third pump. The first treatment device includes a membrane disposed between the body fluid of the first section and the additional fluid of the second section. The circuit can have any of the additional features described above.

In another aspect of the invention, a method for treating a patient with a compromised bodily function includes the steps of providing an extracorporeal circuit, removing a body fluid from the patient, moving the body fluid through a first section of the circuit and moving an additional fluid through a second section of the circuit, and returning processed body fluid to the patient. One circuit is as described immediately above and can have any of the features described above. The method of treating can also have any of the features described above.

In another aspect of the invention, a method for combining two fluids in a treatment device includes the steps of providing a housing that contains a chamber and that contains a plurality of conduits, each conduit having a membrane that defines a lumen and separates the chamber from the lumen of each conduit, and inducing a flow across the membranes from the lumens of the conduits to the chamber. The chamber includes a first inlet and a first outlet and is for containing a first fluid. The first fluid has a first outlet flow rate at the first outlet. The conduits are for containing a second fluid, and the conduits communicate at a second inlet and a second outlet. The second fluid has a second inlet flow-rate at the second inlet. The inducing step can include producing a difference between the first outlet flow rate and the second inlet flow rate such that the first outlet flow rate is greater than the second inlet flow rate.

BRIEF DESCRIPTION OF THE DRAWINGS

The invention, in accordance with preferred and exemplary embodiments, together with further advantages thereof, is more particularly described in the following detailed description, taken in conjunction with the accompanying drawings.

In the drawings, like reference characters generally refer to the same parts throughout the different views. Also, the drawings are not necessarily to scale, emphasis instead generally being placed upon illustrating principles of the invention.

DESCRIPTION

The present invention provides extracorporeal circuits for receiving a body fluid from a patient; treating or processing the body fluid; and returning the body fluid to the patient. Circuits of the invention include a geometry that allows beneficial interconnectivity between shunts, pumps, conduits, and connectors that comprise the circuit. The result of this combination of elements is precise control over fluid flow rate, pressure within the circuit, and temperature of fluid in the circuit.

In a preferred embodiment, a circuit of the invention delivers body fluid from an inlet connected to the patient to a treatment device in the circuit. The circuit includes at least one pump that facilitates flow of body fluid through the circuit. A shunt in the circuit allows fluid to bypass the circuit in the event that the treatment device or some other portion of the circuit becomes blocked or resistant to flow. Additionally, the shunt allows processed body fluid to be recirculated through the extracorporeal circuit in the event that a second circuit to which the extracorporeal circuit is attached becomes blocked or partially blocked. The shunt also provides a position on the extracorporeal circuit that facilitates rapid attachment to and detachment from a second circuit or other components. Pumps associated with the shunt assist in controlling fluid flow via the shunt. Circuits of the invention provide precise control of temperature, pressure, and flow rates through an extracorporeal circuit.

A preferred use of circuits of the invention is for the treatment of a body fluid using one or more treatment devices in serial, fluidic communication with the circuit.

Circuits of the invention are particularly useful with treatment devices such as bioartificial organs. For example, two fluids can be selectively combined across a membrane within the treatment device. Additionally, temperature, pressure, and flow rate can be precisely controlled which allows chemical processes, metabolic processes, and/or other fluid alteration to be performed under optimized conditions.

As used herein, "serial fluidic communication" means that components are ordered one after the next and that they convey and/or help to convey and/or condition a fluid. This definition includes components that contain and/or contact a fluid, components that pump and/or provide a force to a fluid but may not necessarily physically contact a fluid, components which at least partially surround and/or are associated with other components that contain or pump a fluid, components that address or alter a property of a fluid, components that sense a property of a fluid, and/or components regarded by those skilled in the art to be a part of a fluid circuit.

As used herein, "bioartificial organ" means any structure that contains biologically active components that perform, compensate for, or replace one or more body functions.

Figure 1:
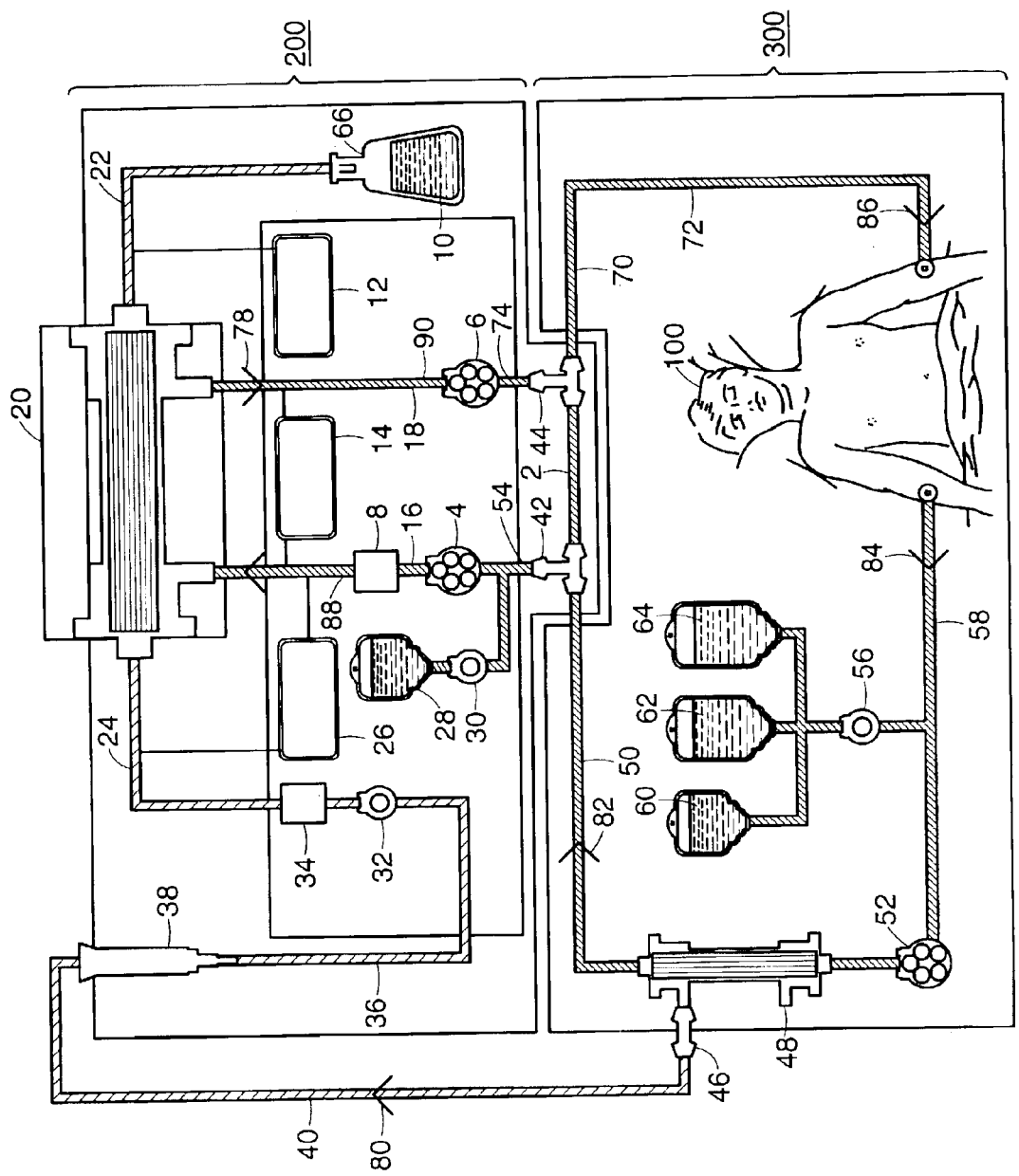
FIG. 1 shows a schematic depiction of one embodiment of an extracorporeal fluid circuit in communication with a hemofiltration circuit.

An extracorporeal circuit of the invention is used alone or in conjunction with other components. Typically, embodiments of the circuit are used with another, existing, circuit. Referring to FIG. 1, one embodiment of a system to treat blood from a patient with compromised renal function is shown. An extracorporeal circuit 200 is connected in line with an existing hemofiltration system 300. The hemofiltration system 300 emerges from a patient's 100 20 venous system in a conduit 58 with a flow direction indicated by numeral 84. The blood is moved in this direction by a blood pump 52. The blood pump 52 can be, for example, but without limitation a roller-type pump. Suitable pumps include the Fresenius Model H Dialysis Machine Blood Pump (Fresenius Medical Care, Lexington, Mass.) and the Gambro Model AK-10 (Gambro Health Care, Stockholm, Sweden). An anticoagulant 60 such as, but without limitation, heparin is infused into the conduit 58 with a pump 56. Many types of IV pumps can be used, such as a Trilogy IV pump (Medex, Inc., Duluth, Ga.). The anticoagulant prevents clotting within the conduits and associated devices. Replacement fluids 62, 64 also are infused into the conduit 58 with a pump 56 to replace blood volume lost as a waste product 10. Alternatively, replacement fluids can be added at any point in the hemofiltration system 300 before the hemofiltration system 300 attaches with the circuit 200. Optionally, the replacement fluids may be heated to a physiological temperature.

Blood then enters a hemofilter 48 where the blood is processed for waste removal in a variety of manners. In the process, a waste, ultrafiltrate, is separated from the blood. After filtration, blood leaves the hemofilter 48 along a blood line 50 in the direction indicated by numeral 82. An optional pump may be included after the hemofilter 48. Blood can continue along a shunt 2 and a conduit 72 in the direction indicated by numeral 86, returning to a patient's 100 arterial system. Also, ultrafiltrate leaves the hemofilter 48 at an ultrafiltrate port 46 and continues along an ultrafiltrate conduit 40 in the direction indicated by numeral 80. An optional pump may be included along the ultrafiltrate conduit 40.

Alternatively, any blood treatment device can be used in the place of the hemofilter 48. For example, but without limitation, a dialyzer or a plasma filter can be used to separate a filtrate component from the blood. These alternatives work by either dialyzing the blood or filtering the blood with a filter capable of excluding particles larger or smaller than those excluded by the hemofilter 48. This filtrate component would contain different minerals, ions, and/or proteins depending upon the process used. The filtrate component would travel through the ultrafiltrate conduit 40.

The hemofiltration system 300 connects with the extracorporeal circuit 200 at three points. First, the ultrafiltrate port 46 connects with the ultrafiltrate conduit 40. Second, the blood line 50 connects with the shunt 2 and a first intake conduit portion 54 at a connector 42. Third, the conduit 72 connects with the shunt 2 and a second outflow conduit portion 74 at a connector 44.

The ultrafiltrate conduit 40 feeds into a drip chamber 38 and then into a conduit 36. The drip chamber 38 separates gases, such as air, from the ultrafiltrate. The drip chamber 38, utilizing gravity, allows air to sit atop the ultrafiltrate as the ultrafiltrate drips into the conduit 36 (fluids generally being heavier than gases). An ultrafiltrate pump 32 and a heat exchanger 34 are positioned after the conduit 36 and before an ultrafiltrate intake conduit 24. The ultrafiltrate intake conduit 24 communicates with a treatment device 20 as well as a pressure monitor 26. An ultrafiltrate line runs from the ultrafiltrate port 46 to the treatment device 20, including all components in between.

The ultrafiltrate pump 32 regulates the ultrafiltrate flow rate from the ultrafiltrate port 46 into the treatment device 20 (e.g., the intercapilary space of a renal assist device). Many types of IV pumps can be used, such as a Trilogy IV pump (Medex, Inc., Duluth, Ga.). The heat exchanger 34 functions to keep ultrafiltrate at a physiological temperature such that any chemical and/or metabolic functions that treatment device 20 carries out can be accomplished. The heat exchanger can be, for example, but without limitation, a water bath at least partially surrounding the ultrafiltrate intake conduit 24.

Ultrafiltrate exits the treatment device 20 through ultrafiltrate outflow conduit 22 and into a waste receptacle 66. The rate of ultrafiltrate exiting the treatment device 20 is determined by the incoming ultrafiltrate rate and the difference in pumping rates between an intake pump 4 and an outflow pump 6 (described in greater detail below). These pumps 4, 6 can be, for example, but without limitation a roller-type pump, such as a Fresenius Model H Dialysis Machine Blood Pump (Fresenius Medical Care, Lexington, Mass.). A flow monitor 12 monitors the ultrafiltrate flow rate in the ultrafiltrate outflow conduit 22. A flow monitor, for example, measures the volume of fluid leaking out of the ultrafiltrate outflow conduit 22 per minute. A flow monitor can have feedback signal function or an alarm function. However, any flow monitor or a medical professional measuring the accumulation of ultrafiltrate over time can be used.

The blood line 50 feeds into either the shunt 2 or the first intake conduit portion 54. An intake line runs from (and includes) the first intake conduit portion 54 to the treatment device 20, including all components in between. An anticoagulant 28, such as, but without limitation, heparin, is infused by a pump 30 into the first intake conduit portion 54 to prevent blood coagulation in the treatment device 20. Alternatively, an anticoagulant can be infused anywhere along the intake line to prevent coagulation within the treatment device 20. Blood entering the intake line is filtered blood from the hemofilter 48 (hereinafter referred to as "blood" or, alternatively, "filtered blood") and it passes through the intake pump 4, into a second intake conduit portion 16, and through a heat exchanger 8. Other embodiments can have unaltered blood or differently altered blood entering the intake line. The heat exchanger 8 functions to keep blood at a physiological temperature such that any metabolic functions that the treatment device 20 carries out can be accomplished. The heat exchanger can be, for example, but without limitation, a water bath at least partially surrounding any portion of the intake line. Then, the blood enters a third intake conduit portion 88 before entering the treatment device 20. Blood flows through the intake line in the direction indicated by numeral 76. Then, blood passes through the treatment device 20 (e.g., the extracapilary space of a renal assist device) and into the first outflow conduit portion 90 in the direction indicated by numeral 78. Blood then passes through an outflow pump 6, the second outflow conduit portion 74, and the connector 44 that connects the shunt 2 with the conduit 72. An outflow line runs from the treatment device 20 to (and including) the second outflow conduit portion 74, including all components in between. A flow monitor 14 measures blood flow rate in the intake and outflow lines. The flow monitor 14 can be a single device, or, alternatively, two or more separate flow monitors. Many flow monitors are suitable for use. The flow monitor 14, monitoring both intake and outflow lines, allows for close regulation of the pump rates of the intake pump 4 and outflow pump 6 and, thus, close regulation of blood flow entering and exiting the treatment device 20. A flow monitor can have a feedback signal function or an alarm function.

A pressure monitor 26 measures blood pressure and/or ultrafiltrate pressure within internal portions of the treatment device 20. The internal portions of the treatment device 20 include a chamber for blood and a chamber for ultrafiltrate, although other treatment devices are contemplated with fewer or more chambers or for holding other fluids. In FIG. 1, the pressure monitor 26 is shown connected to the ultrafiltrate intake conduit 24 and the third intake conduit portion 88. Alternatively, separate pressure monitors can be attached to each position. Generally, the pressure monitor 26 can be connected to any of the ultrafiltrate intake conduit 24, the second intake conduit portion 16, the third intake conduit portion 88, and the first outflow conduit portion 90. Separate pressure monitors can be connected to any or all of these locations. Pressure monitors are generally of the type that are suitable for use in an intensive care unit situation and can have a feedback signal function or an alarm function. For example, the pressure transducer from a Fresenius Model H Dialysis Machine Blood Pump (Fresenius Medical Care, Lexington, Mass.) can be used.

Figure 3:
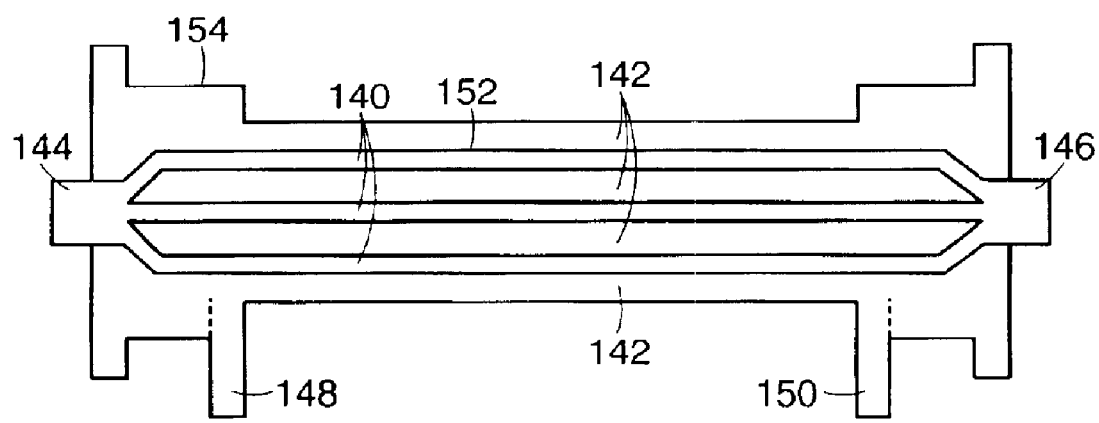
FIG. 3 shows a schematic depiction of one embodiment of a treatment device.

The treatment device 20 can be a bioartificial renal assist device ("RAD") cartridge, as shown in highly schematic fashion in FIG. 3. The RAD cartridge contains a plurality of membranes which are hollow fibers 152 (only one is labeled for clarity) that contain porcine tubule cells cultured in a monolayer on the lining of the lumen 140 of each fiber 152. This luminal space 140 is called the intercapilary space ("ICS"). The ultrafiltrate line is in communication with the lumens 140 of the fibers 152 via an inlet 144. The ultrafiltrate pump 32 maintains ultrafiltrate flow through the ultrafiltrate line and into the lumens 140 (i.e., the ICS) of the fibers 152 within the RAD cartridge. Filtered blood in the intake line enters the RAD cartridge through another inlet 148 and moves into the space 142 surrounding the fibers 152. This surrounding space 142 is called the extracapilary space ("ECS") and is within the housing 154 of the RAD cartridge. The filtered blood and the ultrafiltrate are separate but can be selectively mixed in the ECS, across the membranes, as described below. Alternatively, any two fluids can be mixed between the ICS and the ECS, depending upon the bioartificial organ in use and the relevant body fluids and/or body fluid components. The ultrafiltrate and the filtered blood in the ICS and ECS, respectively, flow concurrently in this embodiment; however, they can flow in a countercurrent manner.

Processed ultrafiltrate, exiting the ICS of the RAD via an outlet 146, enters the ultrafiltrate outflow conduit 22, is collected in the waste receptacle 66, and is discarded as a waste product 10 similar to urine. The filtered blood exits the RAD via another outlet 150 and enters the outflow line. The RAD cartridge is oriented horizontally and placed in a temperature controlled environment. The temperature of the cell compartment of the RAD cartridge is preferably maintained at about 37° C. to about 38° C. throughout its operation to ensure optimal function of the cells. For example, but without limitation, a warming blanket may be used to keep the RAD cartridge at the appropriate temperature. If other bioartificial organs are utilized, different temperatures may be needed for optimal performance.

Blood flow to the circuit 200 is determined by the pumping rate of the hemofiltration pump 52. Some fraction of this blood is diverted through the circuit 200 at the connector 42 and some fraction of this blood will bypass the RAD cartridge in the shunt 2 which runs in parallel with the RAD cartridge and in line with the hemofiltration circuit 300. Each of the blood pump 52, intake pump 4, and outflow pump 6 can be set at different pumping rates. The blood pump 52 may be set, for example, but without limitation, to pump rates from about 100 ml/min to about 500 ml/min, preferably from about 200 ml/min to about 250 ml/min. The intake and outflow pumps 4, 6 can be set, for example, but without limitation, to pump rates from about 50 ml/min to about 200 ml/min, preferably from about 100 ml/min to about 150 ml/min. However, depending upon the treatment device, used, higher or lower flow rates are appropriate including from about 10 ml/min to about 1000 ml/min. For example, a bioartificial organ that replaces the insulin secretory function of the pancreas could function with pumps set at about 10 ml/min, while a combined renal and hepatic treatment could function with pumps set about 1000 ml/min. Typically, the pump rates of the intake pump 4 and the outflow pump 6 differ in an amount from about 5 ml/min to about 20 ml/min, and, typically, the pump rate of the outflow pump 6 is greater than the pump rate of the intake pump 4. Again, depending upon the treatment, larger or smaller differences between the flow rates of the pumps can be used. For example, about a 1 ml/min difference could be used for pancreatic replacement therapy while about a 200 ml/min difference could be used for a combined renal and hepatic replacement therapy. Additionally, flow through the ultrafiltrate conduit 40 is, for example, but without limitation, from about 10 ml/min to about 40 ml/min, and the flow rate through the ultrafiltrate outflow conduit 22 is, for example, but without limitation, from about 8 ml/min to about 30 ml/min, preferably from about 10 ml/min to about 20 ml/min.

The pump rates of the intake pump 4 and the outflow pump 6-should be set such that the ultrafiltrate can be reabsorbed from the ICS to the ECS. Generally, the difference between the pump rate of outflow pump 6 and the pump rate of intake pump 4 determines the reabsorption rate of ultrafiltrate from the ICS, across the membrane, to the ECS. The amount by which the pump rate of outflow pump 6 exceeds the pump rate of intake pump 4, typically, is approximately the reabsorption rate of the ultrafiltrate into the filtered blood. For example, with the blood pump 52 set at 135 ml/min, with the intake pump 4 and the outflow pump 6 set at 80 ml/min and 87 ml/min, respectively, and with the pump rate of the ultrafiltrate pump 32 set to 15 ml/min, about 7 ml/min of ultrafiltrate will be reabsorbed into the ECS and about 8 ml/min of ultrafiltrate will pass into the waste receptacle 66. Additionally, at these settings, flow through the blood line 50 is about 120 ml/min, flow through the shunt 2 is about 40 ml/min, and flow at a portion of a conduit 70, after the connector 44, is about 127 ml/min. Note that this configuration creates a situation where the flow rate out of the RAD cartridge at the outflow line is greater than the flow rate into the RAD cartridge at the ultrafiltrate line. This flow rate difference allows for flow to occur across the membrane (in some embodiments, an osmotic pressure and/or an oncotic pressure also can assist flow across the membrane). Additionally, the intake pump 4 and/or the outflow pump 6 can isolate the RAD cartridge from sudden changes in flow rate and pressure in the hemofiltration circuit 300, a fairly common occurrence in standard designs.

However, the pump rates need not be restricted in this fashion. For example, the pump rates of the intake pump 4 and the outflow pump 6 may be higher than the pump rate of the blood pump 52. With pump rates set in this manner, the blood flows through and is processed in the RAD cartridge. Additionally, retrograde flow through the shunt 2 would occur, such that blood would recirculate through a portion of the circuit 200. Typically, this portion is the intake line, treatment device 20, outflow line, and shunt 2.

When the circuit 200 is initially set up, the hemofiltration circuit 300 is already filtering the patient's 100 blood and ultrafiltrate is being discarded as waste directly from the ultrafiltrate port 46. The intake line and outflow line, portions of which are typically sterile tubing and which may be disposable, as well as the RAD cartridge, are primed before they are attached to the hemofiltration circuit 300. The cell culture media within the RAD cartridge is rinsed out. Then, the RAD cartridge, the intake line, and outflow line are primed with, for example, but without limitation, a heparinized solution to prevent coagulation. Additionally, the ultrafiltration line is primed with, for example, but without limitation, a saline solution. Once the components are free from gasses, such as air, the RAD cartridge is connected to the conduits with aseptic technique.

The blood pump 52 is transiently stopped to cease the flow of blood through hemofiltration circuit 300. This stoppage must be brief in order to prevent coagulation of the blood within the hemofiltration circuit 300. The design of the circuit 200 allows for quick attachment to the hemofiltration circuit 300 during the brief blood pump 52 stoppage. While the blood pump 52 is stopped, the blood line 50 and the ultrafiltrate port 46 are connected with the circuit 200. The shunt 2 is inserted into the hemofiltration circuit 300 with two "T" connectors 42, 44, and the ultrafiltrate conduit 40 is connected to the ultrafiltrate port 46. These connections are made with for example, but without limitation, standard screw-type connectors. These connectors can have a male end that mates with a female end or vice versa. The blood line 50, shunt 2, conduit 72, and ultrafiltrate port 46 may have the corresponding mating part to either the connector or the ultrafiltrate conduit 40 pre-formed into their structure. Alternatively, an adapter with the corresponding mating part may be used. Other connectors also are suitable for this purpose, such as, but without limitation, stop cock valves, as long as they can be quickly secured.

The blood pump 52 then is turned on again. However, the circuit 200 remains "off" while its set-up is being finished, with the blood traveling through the hemofiltration circuit 300 via the shunt 2. No ultrafiltrate or filtered blood is pumped through the circuit 200, other than at the shunt 2, at this point. Thus, while the final equilibration of the circuit 200 takes place, the patient 100 has a constant flow of blood through the hemofiltration circuit 300.

Next, the intake pump 4 and the outflow pump 6 are engaged, preferably simultaneously. Then, the ultrafiltrate pump 32 is engaged and a period of equilibration and pressure monitoring takes place. Some blood continues to flow through the hemofiltration circuit 300 via the shunt 2. As ultrafiltrate and blood flow is initiated through the RAD cartridge, care is taken to ensure that the pressures of the fluids flowing through the device remain within selected limits. For example, but without limitation, suitable pressures through the ICS are from about 0 mm Hg to about 20 mm Hg and preferably about 5 mm Hg, and suitable pressures through the ECS are from about 10 mm Hg to about 50 mm Hg and preferably about 20 mm Hg.

Fluid volume losses and inputs should be monitored throughout the operation of the RAD cartridge within the circuit 200, just as they are monitored in dialysis and hemofiltration. Adjustments may be made to control the net fluid balance. For example, fluid lost as waste 10 is replaced with replacement fluids 62, 64. Typically, the amount of fluids added is equal to the amount of fluids lost as waste.

Excessive clotting and protein build-up in the circuit 200 or hemofiltration circuit 300 can impede flow, cause increases in pressure, and/or can lead to an added resistance or barrier to diffusion which is important for oxygen and nutrient delivery to the cells of the RAD cartridge. Because the ultrafiltrate is in direct contact with the cells lining the fibers of the RAD cartridge, control of its flow rate also is important. Also, hydraulic pressures entering the RAD cartridge, as well as transmembrane pressure gradients, are tightly controlled. Functionality and cell adhesion can be adversely affected if shear forces and pressures are not controlled within allowable levels. For example, if the outflow pump 6 pump rate is too low when compared with the intake pump 4 pump rate, cells can be pushed out of the RAD cartridge and into the ultrafiltrate intake conduit 24.

Moreover, the shunt 2 not only provides a way to quickly connect a portion of the circuit 200 to the hemofiltration circuit 300, but, also, the shunt allows for an alternative fluid pathway if fluid flow is impeded in circuit 200 or hemofiltration circuit 300. For example, if any of the filtered blood in circuit 200 (i.e., in the intake line, RAD cartridge, and/or in the outflow line) is unable to properly flow or the circuit 200 is blocked, filtered blood will shunt through the shunt 2 and only circulate through hemofiltration circuit 300. The patient 100 will not be deprived of blood that is removed from the patient 100 into the conduit 58. Alternatively, if the hemofiltration circuit 300 becomes blocked, blood will recirculate from the second outflow conduit portion 74, through the connector 44, into the shunt 2 (in a retrograde fashion), through the connector 42, into the first intake conduit portion 54, down the intake line, through the RAD cartridge and down the outflow line. Thus, blood will cease to drain from the patient 100 and the filtered blood in the system will continue to circulate through the circuit 200. Along this line of reasoning, valves, and the like, are, typically, not desirable in circuits of the invention because blood and other protein containing fluids can coagulate and/or clog a circuit. Thus, the present invention avoids valves, avoiding this problem, while still maintaining selective fluid flow control and shunting capability.

To discontinue treating a patient 100, replacement fluid is infused into the intake line in the circuit 200 to flush the blood in the circuit 200 into the hemofiltration circuit 300. The intake pump 4 and the outflow pump 6 are turned off, followed by turning off the ultrafiltrate pump 32. Then, the intake line is clamped between the intake pump 4 and the connector 42, and the outflow line is clamped between the outflow pump 6 and the other connector 44. Blood continues to flow through the hemofiltration circuit 300 during this time via the shunt 2 but does not enter the rest of the circuit 200. Then, blood flow through the hemofiltration circuit 300 is stopped transiently; the shunt 2 and connectors 42, 44 are removed; and the blood line 50 is connected with conduit portion 70. Then, the ultrafiltrate line to the ultrafiltrate pump 32 is disconnected. Thus, during the entire process of isolating the circuit 200 from the hemofiltration circuit 300, except for a brief moment to detach the shunt 2 and connect the blood line 50 and conduit portion 70, blood flow is maintained through the hemofiltration circuit 300.

Figure 2:
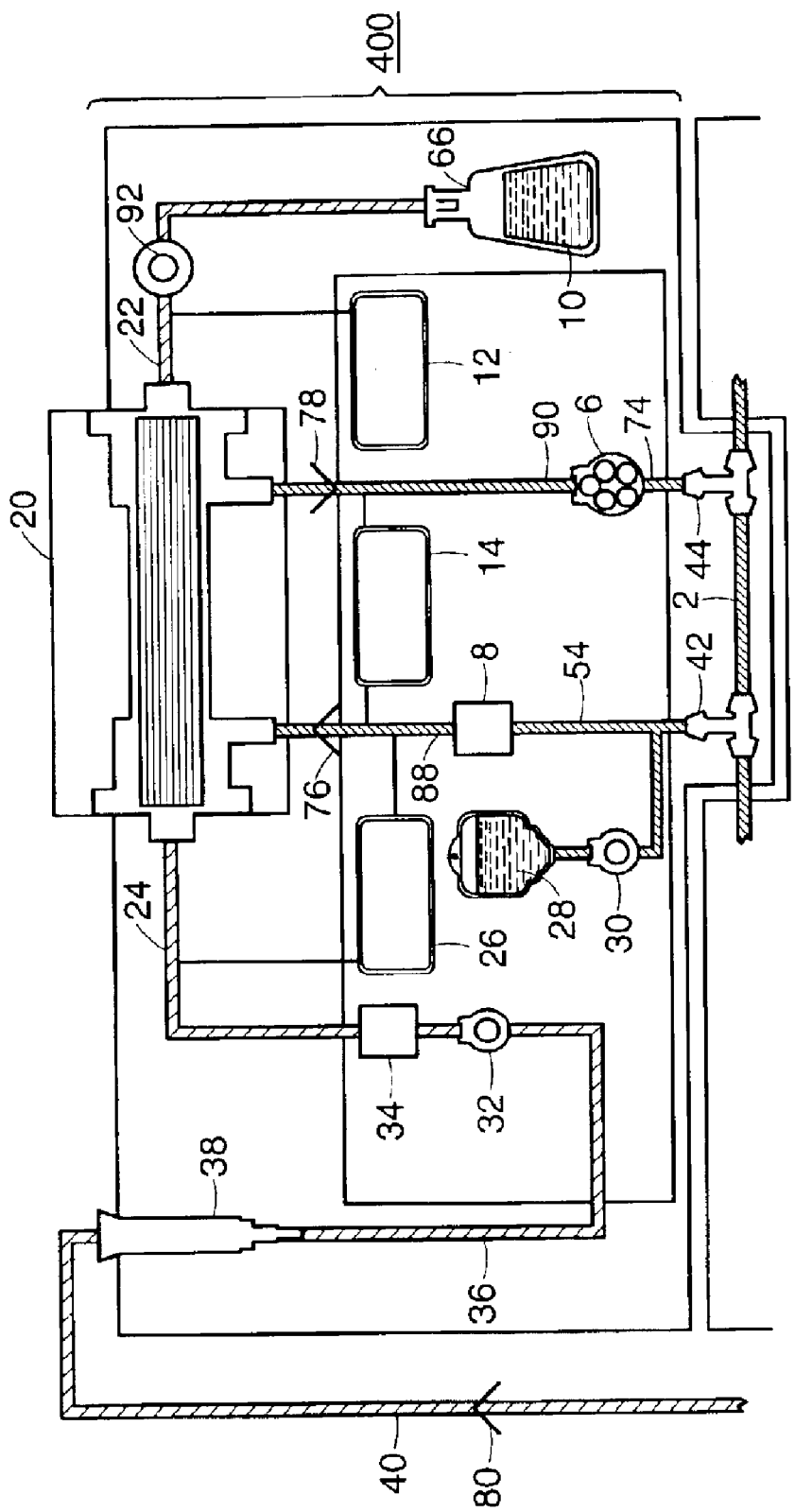
FIG. 2 shows a schematic depiction of an alternative embodiment of an extracorporeal fluid circuit.

Now referring to FIG. 2, an alternative embodiment of an extracorporeal circuit 400, similar to the embodiment in FIG. 1, is shown. Circuit 400 can be connected to, for example, but without limitation, hemofiltration circuit 300 in a manner similar to that of circuit 200. The difference between circuit 400 (FIG. 2) and circuit 200 (FIG. 1) is the pump placement. Instead of the intake pump 4 being located on the inlet line (between the first intake conduit portion 54 and the second intake conduit portion 16), an ultrafiltrate outflow pump 92 is located on the ultrafiltrate outflow conduit 22. In combination with the outflow pump 6 and the ultrafiltrate pump 34, the ultrafiltrate outflow pump 92 is capable of producing a reabsorption from the ICS to the ECS similar to that in circuit 200. Additionally, the shunt 2 could still be used to bypass the circuit 400 if it were to clog and the shunt 2 could be used to recirculate filtered blood if hemofiltration circuit 300 were to clog similar to circuit 200. Note, again, that this embodiment creates a flow differential between the entry point to the ICS and the exit point to the ECS. Additionally, the outflow pump 6 could be moved to a position on first intake conduit portion 54 in this embodiment from the position in which it is shown in FIG. 2.

Figure 4:
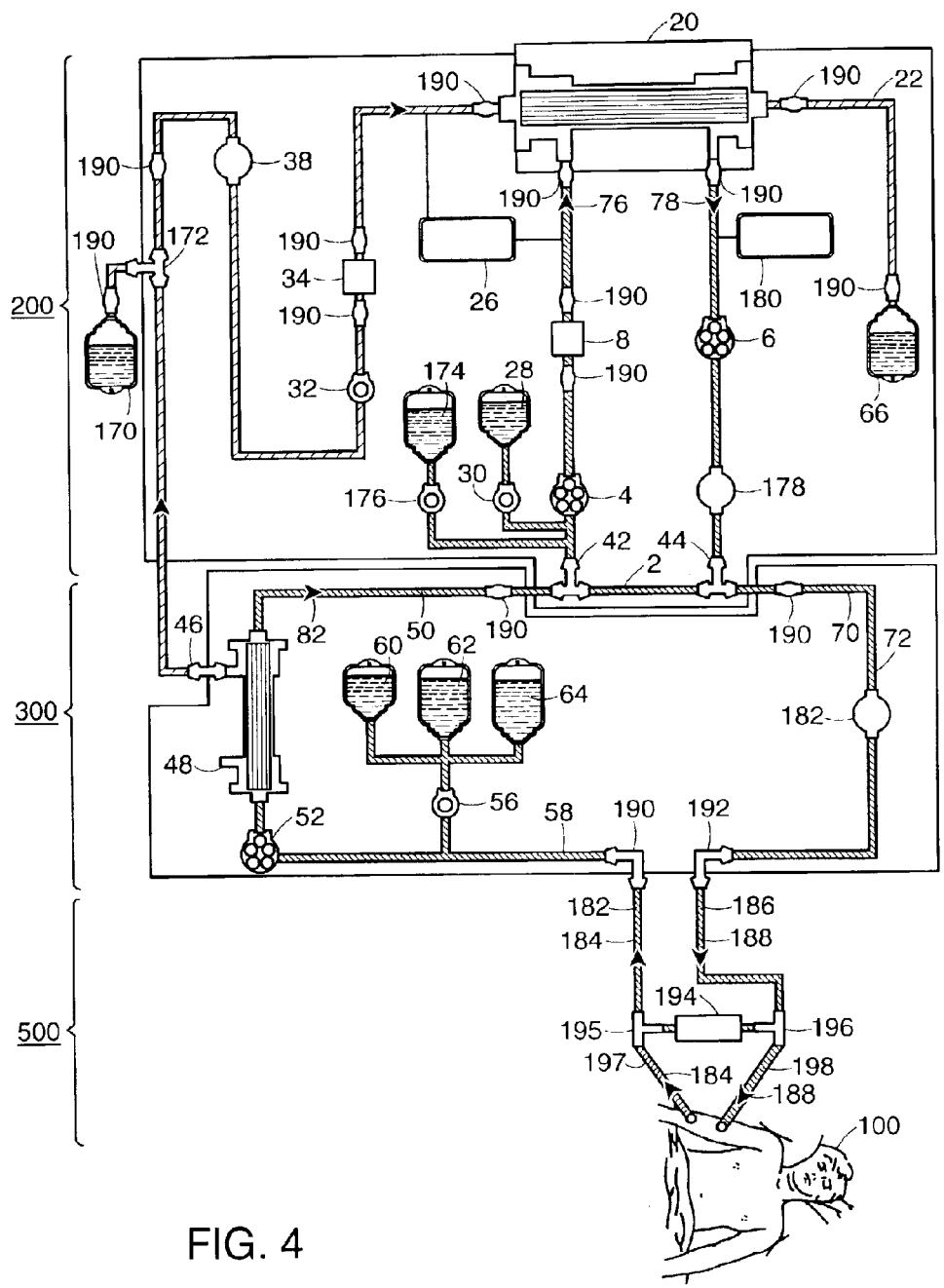
FIG. 4 shows a schematic depiction of one embodiment of an extracorporeal fluid circuit including dialysis lines.

Now referring to FIG. 4, an extracorporeal circuit 200 and a hemofiltration system 300, similar to that shown in FIG. 1, with some modifications, is shown in connection with a highly schematic dialysis circuit 500. Throughout FIG. 4, connectors 190 are drawn which indicate where connectors between conduits or other components of the systems might be located in certain embodiments of the invention, including any embodiments disclosed herein. These locations are intended to be exemplary and are not intended to be limiting. The hemofiltration system 300 is substantially the same as that described for FIG. 1, except that a bubble trap 182 with an air detector is inserted into the conduit 72 after the shunt 2. The bubble trap 182 with the air detector prevents air from circulating in the hemofiltration system 300. If the air detector senses a lack of blood in the bubble trap 182, the air detector triggers a clamp to clamp off the conduit 72.

The circuit 200 also is substantially the same as that described for FIG. 1. However, several items are different.

The ultrafiltrate line includes an ultrafiltrate drain bag 170 in communication with the ultrafiltrate line via a connector 172. The ultrafiltrate drain bag 170 functions to eliminate some of the ultrafiltrate from circulation through the downstream portion of the ultrafiltrate line and the treatment device 20. The ultrafiltrate contains urea and other ureic toxins which some treatment devices 20 cannot remove. Because, in some embodiments, the rate at which ultrafiltrate flows is higher than is necessary in the treatment device 20 but also is desirable for increasing the rate of clearance of toxins from the blood, some ultrafiltrate is removed. Thus, the ultrafiltrate drain bag 170 serves as a point to remove some of the undesired ultrafiltrate before it enters the treatment device 20, and thus eliminate some of the urea and other ureic toxins from the patient. For example, it can be desirable for the ultrafiltrate to flow at about 20 to about 30 ml/min in the ultrafiltrate line upstream from the ultrafiltrate drain bag 170 and to flow at about 5 to about 10 ml/min in the ultrafiltrate line downstream from the ultrafiltrate drain bag 170. In certain embodiments, the flow rate of ultrafiltrate downstream from the ultrafiltrate drain bag 170 is reduced to about a third of the flow rate of the ultrafiltrate upstream from the ultrafiltrate drain bag 170.

Also, replacement fluids 174 are infused by a pump 176 into the intake line. This point of infusion is useful for priming the extracorporeal circuit 200, as described above, or for flushing blood out of the extracorporeal circuit 200, as described above, when detaching the circuit 200 from the hemofiltration system 300. An additional pressure monitor 180 also is included on the outflow line to monitor pressure at that point in the system, and flow monitors 12, 14 also are removed from the system. Generally, in this embodiment, the additional pressure monitor 180 provides a way to measure the pressure difference across the treatment device 20 based on the pressure difference in the intake line and the outflow line. Also, the pumps 4, 6 on the intake and outflow lines have the capability to measure flow, eliminating the need for a separate flow monitor 14 to measure flow in the intake and outflow lines. The flow monitor 12 on the ultrafiltrate outflow line 22 is removed and replaced with a medical professional who measures the accumulation of processed ultrafiltrate over time. Also, a bubble trap 178 is located on the outflow line to prevent delivery of air to the hemofiltration system 300.

The extracorporeal circuit 200 and the hemofiltration system 300 are shown in connection with the dialysis circuit 500. Thus, the blood can undergo dialysis in the dialysis circuit 500, hemofiltration in the hemofiltration circuit 300, and treatment in the extracorporeal circuit 200. However, the hemofilter system 300 is included to generate ultrafiltrate for the ultrafiltrate line and treatment device 20. The hemofiltration system 300 and extracorporeal circuit operate in parallel with the dialysis circuit 500. Additionally, combining these three systems increases the clearance of various materials from a patient's blood. The clearance obtained from the dialysis circuit 500 is added to the clearance from the hemofiltration system 300 and the treatment device circuit 200. Other circuits may be used in addition to or in the place of the dialysis circuit 500.

Typically, the blood from the dialysis circuit 500 enters the hemofiltration system. The dialysis circuit 500 is depicted in highly schematic fashion. Generally, blood travels in a direction indicated by arrow 184 from a patient 100 through a conduit 197 and to a "T" connector 195. At this point, the flow of blood diverges. Some of the blood flows through a dialysis system 194 and some of the blood flows through a pre-dialyser blood conduit 182. The blood in the pre-dialyser blood conduit enters the initial conduit 58 of the hemofiltration system 300 at a connector 190. After processing through the hemofiltration system 300 and the extracorporeal circuit 200, the blood moves through the conduit 72 of the hemofiltration system 300 that is located downstream from the shunt 2 and into a connector 192. The connector 192 connects the hemofiltration system 300 with a conduit 186 that returns the processed blood to the dialysis circuit 500 in the direction indicated by arrow 188. This returning blood enters a connector 196 and mixes with blood that has undergone dialysis in the dialysis circuit 500. The mixed blood then is returned to the patient in a conduit 188 in the direction indicated by arrow 188. Thus, the extracorporeal circuit 200 and the hemofiltration circuit 300 work in parallel with the dialysis circuit 500. In certain embodiments, a dual lumen catheter or two access needles attached to two conduits are inserted into a patient's arterial and venous system. Rather than appearing as is depicted in highly schematic fashion, the dialysis circuit 500 would have a different configuration. However, the dialysis circuit 500 still functions to bring blood to and from the patient, dialysis system, and/or the hemofiltration system 300 in a similar manner to that shown in FIG. 4, with some blood that has not been dialyzed entering the hemofiltration system 200 and with the processed blood from the extracorporeal circuit 200 and hemofiltration system 300 mixing with dialyzed blood before returning to the patient.

Other circuits of the invention are contemplated. These circuits have treatment devices supplying a variety of body functions such as, but not limited to, liver functions, cardiac functions, pancreatic functions, endocrine functions (for example, thyroid function), digestive functions, and combinations thereof. Depending upon the lost functions and other treatments that may be available to help treat those lost functions, different circuits may be appropriate. These circuits will account for other treatments that may be used in conjunction with a bioartificial organ (similar to the role of, although not necessarily the function of, the hemofilter in the embodiments above) and/or link together two or more bioartificial organs. However, these circuits will provide tightly controlled flow, pressure, and/or temperature through the circuit. Additionally, bioartificial organs or other treatment devices that require a controlled flow between two or more compartments are particularly well suited for circuits of the invention. These compartments can contain various fractions of a body fluid, different body fluids, various processed body fluids and/or other exogenous or endogenous fluids. Typically, one or more of these compartments will be connected to circuits with pumps placed in physically or functionally similar locations to those disclosed herein. Additionally, typically, a shunt will be included in the circuit. Thus, functionally, the ability to precisely control temperature, pressure, and flow to provide optimal metabolic and/or chemical conditions, the capability to absorb one fluid into another by controlling pump rates, the ability to shunt fluids in the event of the circuit becoming blocked, and/or the ability to recirculate fluids, in the event components outside of the circuit become blocked, are indicative of some other embodiments of the invention that are contemplated.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A circuit for extracorporeal treatment of a fluid from a body, the circuit comprising:

(a) a first section comprising in serial fluidic communication:
  (1) an inlet for receiving a body fluid from a source;
  (2) a first treatment device for processing the body fluid;
  (3) a first pump;
  (4) an outlet for providing processed body fluid to the body; and
  (5) a shunt, wherein the shunt connects the inlet with the outlet; and (b) a second section comprising in serial fluidic communication:
  (1) a first conduit for receiving an additional fluid from the source;
  (2) a second pump; and
  (3) the first treatment device for processing the additional fluid, wherein the first treatment device comprises a porous member capable of permitting at least a portion of the additional fluid to combine with at least a portion of the body fluid,
  wherein the porous member has a cell located adjacent thereto; and
  wherein the circuit further comprises a third pump between the inlet and the first treatment device in the first section or a third pump after the first treatment device in the second section.

2. The circuit of claim 1 wherein the body fluid is altered prior to entering the inlet.

3. The circuit of claim 1 wherein the shunt connects the inlet to the outlet.

4. The circuit of claim 1 wherein the source comprises a second treatment device and the circuit further comprises the second treatment device upstream from the inlet.

5. The circuit of claim 1 wherein the first treatment device performs at least one function of a human organ.

6. The circuit of claim 5 wherein the first treatment device comprises a renal assist device.

7. The circuit of claim 1 wherein the shunt is in parallel with the first treatment device.

8. The circuit of claim 1 wherein at least a portion of the additional fluid receivable within the first conduit and at least a portion of the body fluid receivable within the inlet combine within the first treatment device.

9. The circuit of claim 1 wherein at least one of the fluids is altered within the first treatment device.

10. The circuit of claim 1 further comprising a waste receptacle in fluidic communication with the first treatment device.

11. The circuit of claim 1 further comprising at least one heating device in association with the circuit.

12. The circuit of claim 1 further comprising an anticoagulant infuser in fluidic communication with the circuit.

13. The circuit of claim 1 wherein at least one of the pumps has a pumping rate from about 10 ml/mm to about 1000 ml/mm.

14. The circuit of claim 1 wherein the first pump has a pumping rate that differs from a pumping rate of the third pump by a value ranging from about 1 ml/min to about 200 ml/min.

15. The circuit of claim 1 wherein the third pump is after the first treatment device in the second section.

16. The circuit of claim 15 further comprising a flow controller between the inlet and the first treatment device in the first section.

17. The circuit of claim 16 wherein the flow controller comprises a pump.

18. The circuit of claim 16 wherein the flow controller comprises a clamp.

19. The circuit of claim 16 wherein the flow controller comprises a pressure monitor.

20. The circuit of claim 1 wherein the body fluid comprises filtered blood.

* * * * *